United States Patent [19]
Janssens et al.

[11] 3,979,394
[45] Sept. 7, 1976

[54] DUPLO QUINOLINE COMPOUNDS

[75] Inventors: Wilhelmus Janssens, Aarschot; Johannes Josephus Vanheertum, Halle-Zandhoven; Albert Lucien Poot, Kontich; Robert Joseph Pollet, Vremde, all of Belgium

[73] Assignee: AGFA-GEVAERT N.V., Mortsel, Belgium

[22] Filed: Mar. 5, 1974

[21] Appl. No.: 448,267

Related U.S. Application Data

[62] Division of Ser. No. 206,872, Dec. 10, 1971, Pat. No. 3,832,171.

[30] Foreign Application Priority Data

Dec. 11, 1970 United Kingdom............. 59094/70

[52] U.S. Cl............. 260/283 BZ; 96/1.5; 96/1.6; 96/1.8; 252/501; 260/240 E; 260/240.1; 260/240.5; 260/240.6; 260/240.65; 260/240.7; 260/283 S; 260/283 R; 260/243 A; 260/243 AA; 260/247.1 A; 260/247.1 L; 260/272; 260/275; 260/289 R
[51] Int. Cl.²...................................... C07D 215/02
[58] Field of Search............... 260/283 BI, 288 CF

[56] References Cited
UNITED STATES PATENTS

| | | | |
|---|---|---|---|
| 2,791,588 | 5/1957 | Collier et al. | 260/283 BI |
| 2,849,452 | 8/1958 | Webb | 260/283 BI |
| 2,947,720 | 8/1960 | Webb | 260/283 BI |
| 3,152,134 | 10/1964 | Humber | 260/283 BI |
| 3,164,599 | 1/1965 | Rapoport | 260/283 BI |
| 3,491,099 | 1/1970 | Copp | 260/283 BI |

OTHER PUBLICATIONS

Mndzhoyan et al.; Chem. Abstr. vol. 59, col. 6362-a; 1963.
Buckmann et al.; Chem. Abstr. vol. 58, col. 3392–3393; 1963.

*Primary Examiner*—Richard J. Gallagher
*Assistant Examiner*—James H. Turnipseed
*Attorney, Agent, or Firm*—William J. Daniel

[57] ABSTRACT

New "duplo" quinoline compounds useful as photoconductors and having the formula:

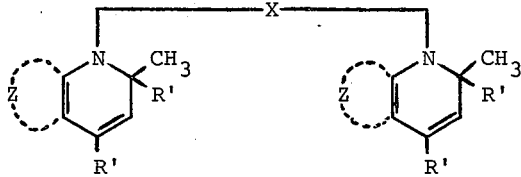

wherein:
Z represents the atoms necessary to close an adjacent aromatic ring,
R' represents a lower alkyl radical, and
X represents an alkylene group or an alkylene group interrupted by a bivalent aromatic group.

2 Claims, No Drawings

DUPLO QUINOLINE COMPOUNDS

This is a division of Ser. No. 206,872, filed Dec. 10, 1971, now U.S. Pat. No. 3,832,171.

This invention relates to recording and reproduction of information-wise modulated electromagnetic radiation and to recording materials suitable therefor, and particularly relates to such processes and recording materials containing one or more organic photoconductive compounds as hereinafter described.

It has now been found that a particularly photosensitive photoconductive recording member can be formed by using in its composition a photoconductive compound corresponding to the following general formula:

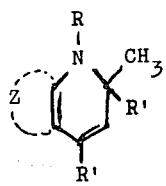

wherein:
R represents an aliphatic radical including a saturated aliphatic radical, an unsaturated aliphatic radical and a cycloaliphatic radical and these radicals is substituted form, preferably an organic group that can be introduced by alkylation for example an alkyl radical including a substituted alkyl radical, e.g. methyl, a cycloalkyl radical, e.g. cyclohexyl, an allyl radical, an aralkyl radical, e.g. benzyl, R' represents a $C_1$–$C_4$ alkyl radical, for example methyl, ethyl, propyl or butyl, preferably methyl, and Z represents the necessary atoms to close an adjacent aromatic nucleus, e.g. a benzene nucleus or an adjacent aromatic ring system including an aromatic nucleus or aromatic ring system substituted with (a) non-ionic substituent(s) e.g. substituted with an alkyl group for example methyl, halogen, for example, F, Cl, Br or I, nitro, an alkoxy group, e.g. methoxy, an amino group, a substituted amino group e.g. a monoalkylamino or dialkylamino group or cyano.

The adjacent aromatic ring system closed by the atoms represented by Z is preferably one of the following unsubstituted or substituted nuclei represented by their structural formula:

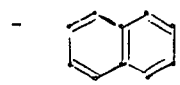 (naphthalene)

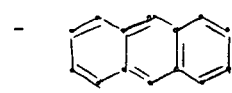 (anthracene)

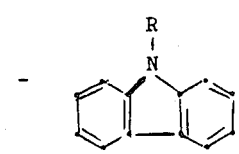 (carbazole)

wherein: R represents hydrogen or an alkyl group e.g. methyl or ethyl.

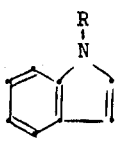 (indole)

wherein: R represents hydrogen or an alkyl group e.g. methyl or ethyl.

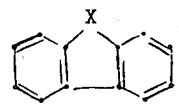 (dibenzofuran)

(dibenzothiophene)

wherein: X represents oxygen or sulphur

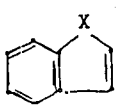 (benzofuran)

(benzothiophene)

wherein: X represents oxygen or sulphur

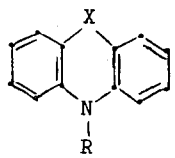 (phenothiazine)

(phenoxazine)

wherein:
X represents oxygen or sulphur, and
R represents hydrogen or an alkyl group e.g. methyl or ethyl.

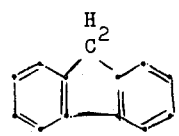 (fluorene)

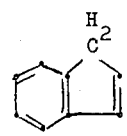 (indene)

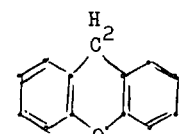 (xanthene)

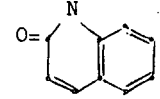 (quinolin-2-one)

wherein:
R is hydrogen or an alkyl group e.g. methyl or ethyl.

Specific examples of monofunctional alkylated 1,2-dihydro-2,2,4-trialkylquinoline compounds are listed in the following Table I.

Table I

| No. | Formula | Melting point, °C |
|---|---|---|
| 1 | | Liquid at room temperature |
| 2 | | 114 |
| 3 | | Liquid at room temperature |

According to a preferred embodiment the photoconductive recording member contains one or more new photoconductive compounds called bifunctional alkylated 1,2-dihydro-2,2,4-trialkylquinoline compounds or "duplo-compounds" corresponding to the following general formula:

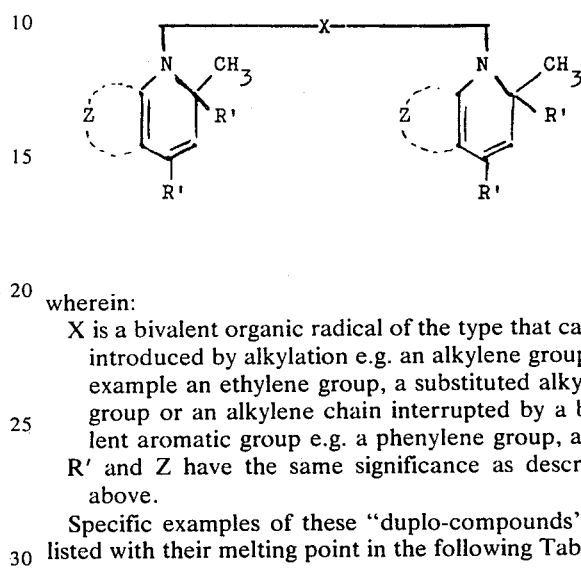

wherein:
X is a bivalent organic radical of the type that can be introduced by alkylation e.g. an alkylene group for example an ethylene group, a substituted alkylene group or an alkylene chain interrupted by a bivalent aromatic group e.g. a phenylene group, and
R' and Z have the same significance as described above.

Specific examples of these "duplo-compounds" are listed with their melting point in the following Table II.

Table II

| No. | Formula | Melting point, °C |
|---|---|---|
| 1 | | 140 |
| 2 | | 199 |
| 3 | | 210 |
| 4 | | 179 |

Table II-continued

| No. | Formula | Melting point, °C |
|---|---|---|
| 5 | | ± 190 |
| 6 | | 171 |
| 7 | | 189 |

The preparation of the intermediate 1,2-dihydro-2,2,4-trialkylquinolines in which R=H proceeds advantageously by condensing an aromatic primary amino compound with an aliphatic ketone containing at least one methyl group linked directly to the carbonyl group of the ketone in a preferred molar ratio of at least 1:2 in the presence of a suitable catalyst, such as toluene sulphonic acid, benzene sulphonic acid, sulphuric acid, iodine or bromine. Examples of suitable ketones are acetones, methyl ethyl ketone, methyl isopropyl ketone methyl butyl ketone, mesityl oxide and diacetone alcohol.

The production of the intermediates is illustrated by the following reaction scheme:

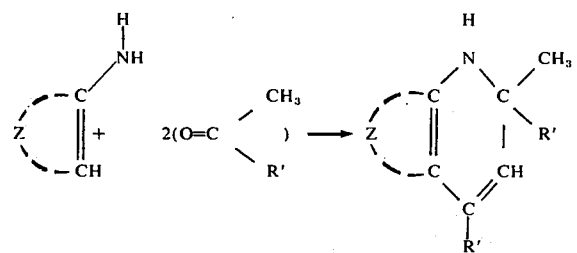

in which Z and R' have the same meaning as described above.

The introduction of the substituent R replacing the hydrogen in the NH group of the 1,2-dihydro-2,2,4-trialkylquinoline may proceed according to known alkylation techniques.

For introducing an alkyl substituent in the 1-position of 1,2-dihydro-2,2,4-trialkylquinoline any suitable alkylating agent e.g. trialkyl phosphates, alkyl iodides, alkyl bromides and alkyl chlorides may be used, the latter preferably in conjunction with a small amount of potassium iodide.

The duplo compounds are advantageously prepared by linking together by alkylation two 1,2-dihydro-2,2,4-trialkylquinolines through the nitrogen atoms in the 1-position.

As suitable bifunctional alkylating agents are mentioned dihalogenated reactants that have the formula Hal-X-Hal in which Hal represents a replacable halogen atom e.g. chlorine, bromine or iodine and X has the same significance as described above.

The following are illustrative of reactants that may be used in the preparation of the duplo-compounds:

ethylene dichloride, dibromide and diiodide
1-chloro-2-bromoethane
propylene dichloride, dibromide and diiodide
trimethylene dichloride, dibromide and bromoiodide
butylene dichloride, dibromide and diiodide
tetramethylene dichloride, dibromide and diiodide
pentylene dichloride, dibromide and diiodide
hexamethylene dichloride, dibromide and diiodide
hexylene dichloride, dibromide and diiodide
octylene dichloride, dibromide and diiodide
pentamethylene dichloride, dibromide and diiodide
alpha, beta-styrene dichloride, dibromide and diiodide
1,2-dibromocyclohexane
1,3-dibromobutane
1,2-dibromobutane
1,4-dichlorobutene-2
2-phenyl-1,2-dibromopropane
1-p-tolyl-1,2-dichloroethane
1,4-di(chloromethyl)benzene
1,4-di(bromomethyl)benzene
1,4-di(iodomethyl)benzene
1-(2,4-dichlorophenyl)-1,2-dichloroethane 1-(p-chlorophenyl)-1,2-dibromoethane
decamethylene dichloride, dibromide and diiodide
dodecamethylene dichloride, dibromide and diiodide
1,2-dibromobutene-3
1,2-dichloropentene-4
1,2-dichloro-3-methylbutene-3
1,4-dichlorobutene-2
1,4-dibromo-2,3-dimethylbutene-2
1,2-dichlorocyclopentene-3
1,4-dibromocyclopentene-2
1,4-dibromo-2,6-dimethylheptene-2
2,3-dichloro-2,6-dimethyloctene-6

Other suitable reactants for the duplo-compound formation are the β-chloroethyl ester of p-tolusulphonic acid and the p-tolusulphonic acid glycol diester.

Preferred reactants are sym.-dibromoethane and sym.-dichloroethane.

The acid produced during the alkylation reaction may be neutralized by any alkaline neutralizing agent ordinarily employed for neutralizing acids produced in condensation reactions e.g. an organic base.

The following preparations illustrate in more details the manufacture of the compounds enumerated in the Tables I and II.

Preparation of compound 1 of Table I

A mixture of 50 g. (0.289 mole) of 2,2,4-trimethylquinoline, 70 ml. (0.58 mole) of trimethyl phosphate and 37.5 g. (0.289 mole) of ethyldiisopropylamine were heated for 24 hr. at 140°C. on an oil bath.

The reaction mixture was poured out in 700 ml. of water and 100 ml. of concentrated ammoniac added. The whole mass was subjected to a steam distillation. The oily product collected in the receiver was dissolved in methylene chloride and dried with anhydrous sodium sulphate. After evaporating the methylene chloride the residue was distilled and the fraction boiling at 132°C. at 8 mm. Hg was collected.
Yield: 90 %.

Preparation of compound 2 of Table I

A mixture of 33.5 g. (0.15 mole) of 2,2,4-trimethyl-7,8-benzo-1,2-dihydroquinoline, 57 g. (0.45 mole) of benzyl chloride and 16 g. (0.15 mole) of sodium carbonate in 300 ml of anhydrous ethanol was kept at reflux temperature for 32 hr.

The obtained reaction product was poured into water and the oily product separated and rubbed with a spatula in a mixture of 1N hydrochloric acid and methanol (volume ratio 1:1). The thus obtained solid product was sucked off and dried under reduced pressure at 50°C. The crude product was crystallized from a mixture of ethylene glycol monomethyl ether and ethanol.
Melting point: 114°C.
Yield: 10 g.

Preparation of compound 3 of Table I

A mixture of 0.29 mole of 2,2,4-trimethyl-7,8 benzo-1,2-dihydroquinoline, 70 ml. of trimethyl phosphate and 0.29 mole of ethyldiisopropylamine was heated with stirring for 24 hr. on an oil-bath of 140°C.

The obtained reaction product was poured into a mixture of 700 ml. of water and 100 ml. of concentrated ammonium hydroxide. The whole mixture was subjected to an extraction with methylene chloride. The extract was dried over anhydrous sodium sulphate and after filtering the solvent evaporated.

The residue was distilled with fractionating column under diminished pressure. The fraction boiling between 138°–142°C at 1 mm. Hg and between 131°–133°C. at 0.6 mm. Hg was collected and identified as Compound 3 of Table 1. Yellow fluorescing oil.
Yield: 25 g.

preparation of Compound 1 of Table II

A mixture of 8.65 g. (0.05 mole) of 2,2,4-trimethyl-1,2-dihydroquinoline, 8.6 ml. (0.1 mole) of 1,2-dibromoethane and 11.7 g. (0.063 mole) of triisopropanolamine was heated for 3 days on an oil bath of 100°C.

The obtained reaction mass was transferred in chloroform and washed first with 1N hydrochloric acid and thereupon with water. The chloroform was evaporated and the residue left rubbed with a spatula in methanol. The crude product was recrystallized from n-butanol.
Yield : 5 g
Melting point : 140°C.

Preparation of Compound 2 of Table II

A mixture of 108.5 g. (0.5 mole) of 2,2,4-trimethyl-6-ethoxy-1,2-dihydroquinoline, 6.6 g. (0.35 mole) of dibromoethane and 96 g. (0.5 mole) of triisopropanolamine was heated for 32 hr. at 100°C. on an oil bath.

The reaction mixture was dissolved in chloroform and washed first with 1N hydrochloric acid and thereupon with water. The chloroform was evaporated and the oily residue left rubbed with a spatula in acetonitrile. The formed solid was separated and washed with diethyl ether.

Crystallization from acetonitrile in the presence of active coal yielded said compound melting at 199°C.
Yield : 34 g.

Preparation of Compound 3 of Table II

A mixture of 47.75 g (0.25 mole) of 2,2,4-trimethyl-6-fluoro-1,2-dihydroquinoline, 42.75 g. (0.18 mole) of the p-toluene sulphonic acid ester of β-chloroethanol and 48 g. (0.25 mole) of triisopropanolamine was heated for 32 hr. at 100°C. on an oil bath.

A reaction mixture was dissolved in chloroform and washed first with 1N hydrochloric acid and thereupon with water. The chloroform was evaporated and the oily residue left rubbed with a spatula in methanol.

The product was purified by crystallization from ethylene glycol monomethyl ether.
Melting point : 210°C.
Yield : 12 g.

Preparation of Compound 4 of Table II

A mixture of 95 g. (0.5 mole) of 2,2,4,6-tetramethyl-1,2-dihydroquinoline, 96 g. (0.5 mole) of triisopropanolamine (0.5 mole) and 32 ml. (0.36 mole) of dibromoethane was heated for 3 days at 100°C. on an oil bath.

The reaction mixture was dissolved in chloroform and washed with 1 n hydrochloric acid and thereupon with water. The chloroform was evaporated and the oily residue left rubbed with a spatula in methanol. The solid was crystallized from ethylene glycol monomethyl ether in the presence of active carbon and the crystalline product sucked off and washed with ether.
Melting point : 179°C.
Yield : 55 g.

Preparation of Compound 5 of Table II

A mixture of 16 g. (0.06 mole) of 2,2,4-trimethyl-1,2-dihydro-10H-indeno[1,2-g]quinoline, 29.4 ml. (0.15 mole) of the p-tolusulphonic acid ester of β-chloroethanol and 13.5 ml. (0.075 mole) of ethyldiisopropylamine was heated for 32 hours at 100°C. on an oil bath.

The reaction mixture was dissolved in chloroform and washed first with 1N hydrochloric acid and thereupon with water. The chloroform was evaporated and the oily residue left rubbed with a spatula in methanol. The solid product thus obtained was introduced in boiling ethanol and the solid left sucked off and dissolved in ethanolic hydrogen chloride solution which was neutralized with ethanolic potassium hydroxide solution. The separated solid product was thoroughly washed with water.

Melting point : ± 190°C.
Yield : 10 g.

Preparation of Compound 6 of Table II

A mixture of 100.5 g. (0.5 mole) of 2,2,4,6,7-pentamethyl-1,2-dihydroquinoline, 96 g. (0.5 mole) of triisopropanolamine and 32 ml. (0.36 mole) of dibromoethane was heated for 3 days at 100°C. on an oil bath.

The reaction mixture was dissolved in chloroform and washed first with 1N hydrochloric acid and thereupon with water.

The chloroform was evaporated and the residue left introduced in methanol and filtered over active coal. The filtrate was diluted with water until turbidity and the starting of crystallization. The separated solid was recrystallized from acetonitrile.

Melting point: 171°C.
Yield : 46 g.

Preparation of Compound 7 of Table II

A mixture of 17.3 g. (0.1 mole) of 2,2,4-trimethyl-1,2-dihydroquinoline, 8.75 g. (0.05 mole) of 1,4-di(-chloromethyl)-benzene and 19.1 g. (0.1 mole) of triisopropanolamine was heated with stirring for 5 hours on an oil bath at 125°C.

The reaction mass was cooled, and ground in a mortar. The powder thus obtained was washed first with 1N hydrochloric acid and thereupon with water till pH 7. The product was dried and recrystallized from acetonitrile.

Yield : 15 g.
Melting point : 189°–190°C.

The photoconductive compounds applied according to the present invention may be used alone or in combination with substances imparting desired chemical or physical properties to the recording element. So, these substances can be combined with other substances that either or not are photoconductive and exert an influence e.g. on the dark-resistivity, the dischargeability or conductivity of the recording layer by an exposure to electromagnetic radiation, or on the transparency or the quality of the final image, e.g. by counteracting the fringe effect as described in the United Kingdom patent specification No. 1,007,349 filed Oct. 12, 1961 by Gevaert Photo-Producten N.V.

A proper combination with selected binding agents and/or chemical sensitizing agents may result in an enhancement of the total sensitivity. The recording elements according to the present invention preferably contain at least 5% by weight of a photoconductive 1,2-dihydroquinoline derivative being within the scope of the above general formulae. For use in electrophotography the recording element preferably consists for at least 10% by weight of one or more of the said 1,2-dihydroquinoline derivatives. The electrically insulating binding agent used in a recording layer containing said derivative may provide the desired mechanical strength for instance to form a self-supporting layer, and preferably has a resistivity of at least $10^9$ ohm.cm.

According to a particular embodiment the recording layer consists of the photoconductor, which, e.g., has been applied to a suitable support in molten state forming a micro-crystalline or glass-like layer on cooling. This technique can be applied when the photoconductive recording element has not to possess a high mechanical strength. For such technique reference is made to the Canadian patent specification 712,541 filed Feb. 5, 1960 by Gevaert Photo-Producten N.V.

Macromolecular compounds suitable for use as insulating binding agent for the photo-conductive compounds are, e.g., natural resins such as dammar resin, gum arabic, microcrystalline waxes, modified natural substances such as cellulose diacetate, cellulose triacetate, and ethyl cellulose, pentaerythrite polyesters or modified colophony resins and ester gums, polymers such as polyethylene, polystyrene and copolymers of styrene, polyvinyl acetate and copolymers of vinyl acetate, polyvinyl acetals of formaldehyde, acetaldehyde or butyraldehyde, polyacrylic acid esters and polymethacrylic acid esters, coumarine-indene resins epoxy resins and polycondensates such as glycerol-phthalate resins and other glyceryl polyesters, alkyd resins, diethylene glycol polyesters, formaldehyde resins and silicone resins.

Preferred binding agents are halogen-containing polymers. The sensitization of organic photoconductors with halogen-containing polymers is described in the United Kingdom patent specification 964,878 filed May 3, 1960 by Gevaert Photo-Producten N.V. According to said specification a material suitable for use in electrophotography comprises a photoconductive layer incorporating an organic monomeric photoconductor and a halogencontaining polymer in such layer or in a juxtaposed layer (if any), the sensitivity of said photoconductor having been increased by making it to interact with said halogen-containing polymer by heating.

In the following Table III a list of preferred polymeric binding agents is given, which may be used in combination with the heterocyclic organic photoconductors of use according to the present invention as well as the corresponding suitable solvents.

Table III

| Polymeric binding agent defined by its structural unit(s) | Solvent |
|---|---|
| 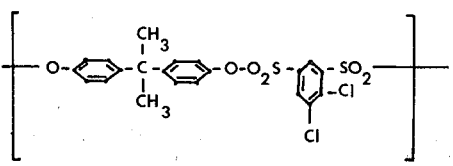 | methylene chloride |

Table III-continued
| Polymeric binding agent defined by its structural unit(s) | Solvent |
|---|---|
| 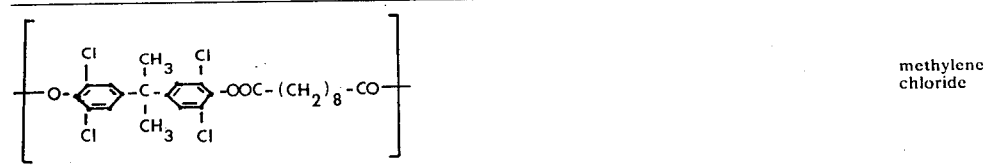 | methylene chloride |
| 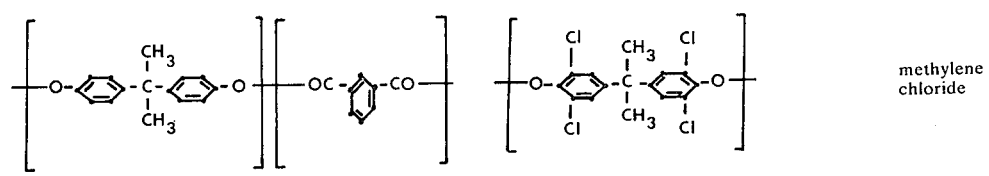 | methylene chloride |
|  | methylene chloride |
| 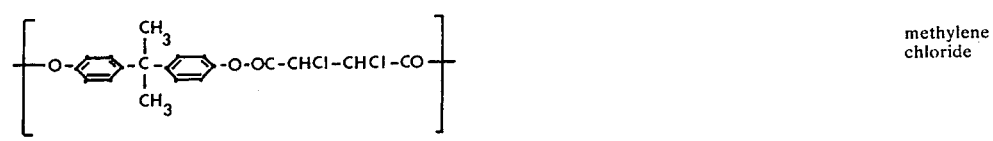 | methylene chloride |
|  | methylene chloride |
| 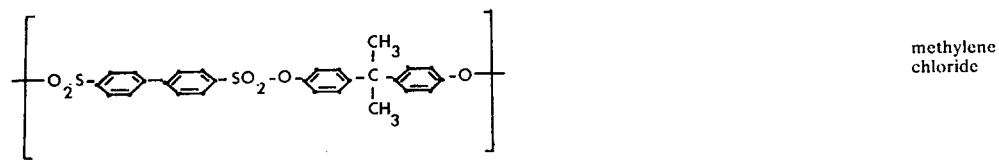 | methylene chloride |
|  | methylene chloride |
|  | methylene chloride |
|   25 % by weight | methylene chloride |

Table III-continued

| Polymeric binding agent defined by its structural unit(s) | Solvent |
|---|---|
| $\left[ -CH_2-CH- \atop \phantom{xx} O \atop \phantom{xx} CO \atop \phantom{xx} CH_3 \right]$ | methylene chloride |
| $\left[ -CH_2-\underset{\underset{n-C_4H_{10}}{\underset{O}{CO}}}{\overset{CH_3}{C}}- \right]$ | methylene chloride |
| $\left[ -CH_2-CH-CH_2-CH- \atop \phantom{xxx} O \diagdown \phantom{xx} O \atop \phantom{xxxxx} CH \atop \phantom{xxxxx} CH_3 \right]$ | methylene chloride |
| | methylene chloride |

10% by weight — 80% by weight — 10% by weight $\left[ -CH_2-CH- \atop \phantom{xx} \bigcirc \right]$  $\left[ -CH_2-CH- \atop \phantom{xxx} NCarbazole \right]$  $\left[ -CH_2-CH- \atop \phantom{xxx} CN \right]$ methylene chloride/acetone (1:1)

91% by weight — 3% by weight — 6% by weight $\left[ -CH_2-CH- \atop \phantom{xx} Cl \right]$  $\left[ -CH_2-CH- \atop \phantom{xx} O \atop \phantom{xx} CO \atop \phantom{xx} CH_3 \right]$  $\left[ -CH_2-CH- \atop O=C \diagdown C=O \atop \phantom{xxx} O \right]$ methylene chloride acetone (1:4)

85% by weight — 14% by weight — 1% by weight $\left[ \begin{array}{c} (CH_2)_2-CH_3 \\ CH\!-\!\!-\!\!O \\ O \diagdown \phantom{xx} CH- \\ -CH_2-HC\!-\!\!-\!CH_2 \end{array} \right]$ methylene chloride acetone ethanol (1:1:1)

The photoconductive compounds applied according to the present invention can be used in admixture with other known inorganic and organic photoconductive substances, e.g. sulphur, selenium, photoconductive oxides, sulphides, and selenides of zinc, cadmium, mercury, antimony, bismuth, lead, anthracene, anthraquinone, and photoconductive polymers e.g. those containing N-vinylcarbazole recurring units and other known monomeric and polymeric organic photoconductors, e.g. those described in the published Dutch patent application No. 70/04174 filed Mar. 24, 1970 by Gevaert-Agfa N.V.

The inherent spectral sensitivity of most of the photoconductive compounds listed in Tables I and II is mainly situated in the near U.V. range, i.e. in the range of 360 to 420 nm.

The spectral sensitivity of recording materials according to the present invention can be increased in different ways, e.g. by adding so-called spectral sensitizing agents for the photoconductive substances contained in the recording element or by admixing to the said heterocyclic organic photoconductive compounds other photoconductive substances, the inherent sensitivity of which for a particular part of the electromagnetic radiation spectrum is higher than that of the present compounds.

So, according to a special embodiment of the present invention semi-transparent recording layers are prepared, in which said heterocyclic photoconductive compounds are used in admixture with at least one inorganic photoconductive substance, especially photoconductive substances of the group of zinc oxide, photoconductive lead(II) oxide and photoconductive cadmium sulphide or cadmium selenide.

Suitable spectral sensitizing dyestuffs for the organic photoconductor are among others organic dyestuffs, known as methine dyes, or xanthene dyes of which the phthaleins and rhodamines are subclasses, and triarylmethane dyes e.g. crystal violet (C.I. 42,555) and the triarylmethane dyes described in published Dutch patent application Nos. 6704706 filed Apr. 3, 1967 by Gevaert-Agfa N.V. The term methine dyes includes mono- as well as polymethine dyes which dyes are known to those skilled in the art of the spectral sensitization of light-sensitive silver halide. Preferred methine dyes are of the cationic type. As preferred xanthene dyes Rhodamine B (C.I. 45,170), Rose Bengale (C.I. 45,440) and Fluorescein (C.I. 45,350) are mentioned. The spectral sensitizing dyes are preferably added to the recording layer composition in a proportion of 0.01 to 5% by weight in respect of the photoconductive substance(s).

Particularly preferred methine dyes are within the scope of the following general formulae :

I.

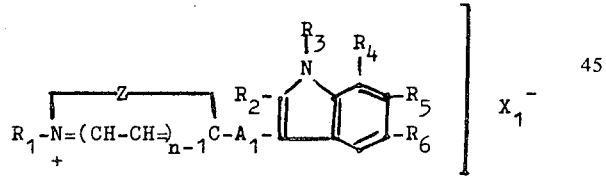

wherein :

A₁ stands for a dimethine or tetramethine group including a substituted dimethine or tetramethine group, n stands for 1 or 2, R₁ stands for alkyl including substituted alkyl, an unsaturated aliphatic group e.g. allyl, aralkyl including substituted arakyl, aryl including substituted aryl or cycloalkyl, R₂ stands for alkyl, aryl including substituted aryl, e.g. phenyl and phenyl substituted preferably in the p-position by alkyl, halogen and alkoxy, a 5- or 6-membered heterocycle the heteroatom of which is oxygen, sulphur, selenium or nitrogen such as 2-, 3-, or 4-pyridyl, 2-furyl, 2-thienyl, etc. including their quaternary salts, R₃ stands for hydrogen or has one of the meanings given for R₁, R₄ stands for hydrogen, alkyl, alkoxy or halogen or together with R₃ forms an alkylene bridge such as dimethylene and trimethylene, each of R₅ and R₆ (the same or different) stands for hydrogen, alkyl, alkoxy or halogen or together represent the atoms necessary to complete a fused-on benzene nucleus;

X₁ represents an anion e.g. Cl⁻, Br⁻, I⁻, ClO₄⁻, CH₃SO₄⁻, or

but is missing when the R₁ group contains already an anion (betaine type salt), and Z represents the atoms necessary to complete a heterocyclic nucleus of the types used in the production of cyanine dyes e.g. such as those of the thiazole series e.g. thiazole, 4-methylthiazole, 4-methyl-5-carbethoxythiazole, 4-phenylthiazole, 5-methylthiazole, 5-phenylthiazole, 4-(p-tolyl)-thiazole, 4-(p-bromophenyl)-thiazole, 4,5-dimethylthiazole, 4,5-diphenylthiazole, 4-(2-thienyl)-thiazole, 4-(m-nitrophenyl)-thiazole, those of the benzothiazole series, e.g. benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 6-sulphobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, 4,5,6,7-tetrahydrobenzothiazole, 5,6-dimethoxybenzothiazole, 5,6-dioxymethylenebenzothiazole, 5-hydroxybenzothiazole, 6-hydroxybenzothiazole, 5,6-dimethylbenzothiazole, those of the naphthothiazole series e.g. naphtho[2,1-d]thiazole, naphtho [1,2-d]thiazole, 5-methoxynaphtho[1,2-d]-thiazole, 5-ethoxynaphtho[1,2-d]-thiazole, 3-methoxynaphtho[2,1-d]-thiazole, 7-methoxynaphtho[2,1-d]-thiazole, those of the thionaphtheno [7,6-d]-thiazole series e.g. 7-methoxythionaphtheno[7,6-d]-thiazole, those of the thiadiazole series e.g. 4-phenylthiadiazole, those of the oxazole series e.g. 4-methyloxazole, 5-methyloxazole, 4-phenyloxazole, 4,5-diphenyloxazole, 4-ethyloxazole, 4,5-dimethyloxazole, 5-phenyloxazole, those of the benzoxazole series e.g. benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 5-methoxybenzoxazole, 6-methoxybenzoxazole, 5-hydroxybenzoxazole, 6-hydroxybenzoxazole, those of the naphthoxazole series, e.g. naphtho[2,1-d]oxazole, naphtho[1,2-d]oxazole, those of the selenazole series e.g. 4-methylselenazole, 4-phenylselenazole, those of the benzoselenazole series e.g. benzoselenazole, 5-chlorobenzoselenazole, 5-methoxybenzoselenazole, 5-methyl-6-methoxybenzoselenazole, 5,6-dioxymethylenebenzoselenazole, 5-hydroxybenzoselenazole, 4,5,6,7-tetrahydrobenzoselenazole, those of the naphthoselenazole series e.g. naphtho[2,1-d]selenazole, naphtho[1,2-d]selenazole, those of the thiazoline series e.g. thiazoline, 4-methylthiazoline, 4-hydroxymethyl-4-methylthiazoline, 4,6-bis-hydroxymethylthiazoline, those of the oxazoline series e.g. oxazoline, those of the selenazoline series e.g. selenazoline, those of the 2-quinoline series e.g. quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline, 8-hydroxyquinoline, etc., those of the 4-quinoline series e.g. quinoline, 6-methoxyquinoline, 7-methylquinoline, 8-methylquinoline, those of the 1-isoquinoline series e.g. 1-isoquinoline, 3,4-dihydroisoquinoline, those of the 3-isoquinoline series e.g. 3-isoquinoline, those of the pyrimidine series, those of the quinoxaline series, those of the quinazoline series, those of the 1-phthalazine series, those of the 2-pyridine series, e.g. pyridine, 5-methylpyridine, 3-nitropyridine, those of the 3,3-dialkylindolenine series, e.g. 3,3-dimethylindolenine, 3,3,5-trimethylindolenine, 3,3,7-trimethylindolenine, etc., those of the benzimidazole series e.g. benzimidazole, 5,6-dichlorobenzimidazole, 5-chlorobenzimidazole, 5,6-dibromobenzimidazole, 5-chloro-6-amino-benzimidazole, 5-chloro-6-bromobenzimidazole, 5-phenylbenzimidazole, 5-fluorobenzimidazole, 5,6-difluorobenzimidazole, 5-cyanobenzimidazole, 5,6-dicyanobenzimidazole, 5-chloro-6-cyanobenzimidazole, 5-fluoro-6-cyanobenzimidazole, 5-acetylbenzimidazole, 5-chloro-6-fluorobenzimidazole, 5-carboxybenzimidazole, 7-carboxybenzimidazole, 5-carbethoxybenzimidazole, 7-carbethoxybenzimidazole, 5-sulphamylbenzimidazole, or 5-N-ethylsulphamylbenzimidazole, 5-ethylsulphonylbenzimidazole and 5-trifluoromethylsulphonylbenzimidazole;

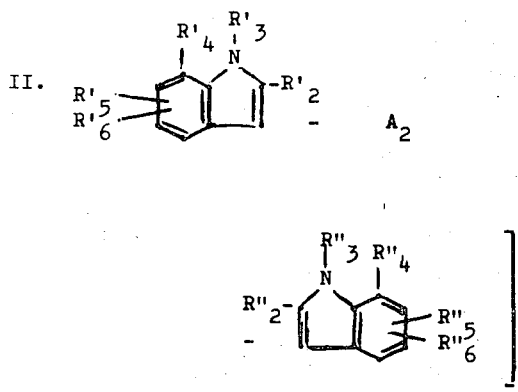

wherein:
$A_2$ stands for a monomethine or trimethine group including a substituted monomethine or trimethine group, each of $R'_2 - R'_6$ and $R''_2 - R''_6$ (the same or different) has one of the meanings given for $R_2 - R_6$,
$X_2^-$ has the same significance as $X_1^-$;

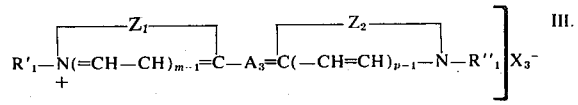

wherein:
each of $R'_1$ and $R''_1$ (the same or different) has one of the meanings given for $R_1$,
$X_3^-$ has the same meaning as $X_1^-$,
$A_3$ has the same meaning as $A_2$;
each of $m$ and $p$ (the same or different) stands for 1 or 2, and
each of $Z_1$ and $Z_2$ (the same or different) stands for the atoms necessary to complete a heterocyclic nucleus of the thiazole, benzothiazole, naphthothiazole, thionaphtheno[7,6-d]-thiazole, thiadiazole, oxazole, benzoxazole, naphthoxazole, selenazole, benzoselenazole, naphthoselenazole, 2-quinoline, 4-quinoline, pyrimidine, quinoxaline, quinazoline, 2-pyridine, 3,3-dialkylindolenine or of the benzimidazole series;
representative examples of these heterocyclic nuclei can be found above in the definition of Z in formula I.

The dyestuffs corresponding to the above general formulae can be prepared according to the methods known by those skilled in the art of methine dye chemistry.

According to a further embodiment of the invention, the recording material contains one or more substances that increase the photoconductivity of the recording material in the inherent spectral sensitivity range of the said heterocyclic organic photoconductive compounds. As already has been said a binding agent can act as a sensitizing agent that enhances the total sensitivity of the recording element. In addition are to be mentioned compounds containing one or more electron-attracting atoms or groups, e.g. those that are known as non-ionic Lewis acids, e.g. the Lewis acids that can form a "charge transfer complex" as described in U.S. Pat. No. 3,408,183 of Joseph Mammino issued Oct. 29, 1968. Good sensitizing results are obtained with organic carboxylic acid anhydride compounds and with quinones containing electron-attracting substituents, e.g. halogen or cyano, such as in tetrachlorobenzoquinone, tetracyanobenzoquinone and in organic compounds containing a

group, and with the compounds according to the structural formula of the Belgian patent specification No. 734,141 filed June 6, 1969 by Gevaert-Agfa N.V. and the chlorine- and/or cyano-containing polymers of Table III.

The 1,2-dihydroquinoline derivatives may be used in admixture with diazonium salts that on exposure to electromagnetic radiation produce at least one radical that irreversibly increases the electro-conductivity of a recording layer. Such substances as well as details about their incorporation into a recording layer containing an organic photoconductive insulating substance are described in the United Kingdom patent specification No. 964,872 filed Apr. 22, 1959 by Gevaert Photo-Producten N.V. and the U.S. Pat. No. 3,113,022 of Paul Maria Cassiers, Jean Marie Nys, Jozef Franz Willems and René Maurice Hart issued Dec. 3, 1963. A particularly suitable conductivity-increasing diazonium compound is p-nitrobenzenediazonium chloride. The diazonium compounds are preferably used in an amount of 0.01 % to 10 % by weight in respect of the present photoconductive heterocyclic organic compounds.

Other additives well known in the art of preparing photoconductive coatings for recording purposes may be used, e.g. matting agents, fluorescing compounds, phosphors, optical brightening agents, agents controlling the adhesive power of the recording layer, agents controlling the elasticity, the plasticity and the hardness of the recording layer, agents controlling the viscosity of the coating composition, antioxidants, gloss-improving agents, etc.

Transparent and semi-transparent recording materials containing the photoconductive heterocyclic organic compounds as described hereinbefore are especially suited for use in recording materials applied for the production and reproduction of microfilm images. Microfilm images can be copied in contact or enlarged optically on recording materials according to the present invention. According to the type of development, the transparencies obtained (contact copies and enlargements) can serve as negative or positive intermediate prints for further printing, e.g. on diazotype materials.

The semitransparent recording materials according to the present invention preferably have an optical density not larger than 0.30 towards visible light or the copying light used in the printing apparatus wherein it is used as intermediate print.

The photoconductive heterocyclic organic compounds described hereinbefore are further especially suited for being applied in the manufacture of pigment images wherein the latter may have the properties of a fluorescent compound or phosphor. As is generally known luminescent phosphors are used in screens of cathode-ray tubes and more particularly in television, X-ray, radar and oscilloscope screens.

In colour television screens phosphors of different colour have to be fixed on a screen in a particular pattern.

The described photoconductive compounds are successfully used in a process for the production of colour television screens as described in the French patent specification No. 1,336,499 filed Sept. 26, 1962 by Comp. Francaise Thomson-Houston. According to the process described in said specification a pattern of a phosphor on a screen support is produced by the steps of applying to said support a coating of an electroconductive material and to said coating a layer comprising a vaporisable or thermolysable photoconductive compound optionally incorporated in a vaporisable or thermolysable binding agent. On said coating an electrostatic charge pattern corresponding with the pigment pattern to be produced is formed electrophotographically, and the electrostatic charge pattern is developed with non-volatile powder particles that have the desired phosphorescent or luminescent properties. Subsequently the photoconductive layer containing the phosphor powder image is heated in order to remove the volatile substances of the photoconductive recording layer and to make the phosphor pattern adhere to the screen support.

In order to fix the powder image before applying the heating step it is preferably overcoated with a layer of thermolysable binding agent.

According to said French Patent Specification photoconductors of the group of anthracene, anthraquinone and xanthene are used. The recording layer may further contain boric acid.

The photoconductors mentioned in the French Patent Specification No. 1,336,499 are advantageously partly or wholly substituted by the photoconductive substances applied according to the present invention.

Suitable thermolysable binding agents belong to the class of the polyacrylic acid esters and polymethacrylic acid esters, e.g. polymethyl methacrylate, polyethyl methacrylate and polyethyl acrylate.

The thickness of the photoconductive layers of the present invention is not critical but is open to choice within a wide range according to requirements in each individual case. Good results are attained with photoconductive layers of a thickness between 1 and 30 mu preferably between 2 and 20 mu. Too thin layers do not have a sufficient insulating power in the absence of active electromagnetic radiation, whereas too thick layers require extensive exposure times.

In the manufacture of electrophotographic recording materials according to the present invention a relatively conductive support for the recording layer is used, e.g. an electroconductive sheet or plate, or an insulating sheet or plate covered with an electro-conductive interlayer. By electro-conductive plate or sheet is understood a plate or sheet whose electrical resistivity is smaller than that of the non-irradiated (dark-adapted) photoconductive layer i.e. in general smaller than $10^9$ ohm.cm and preferably is at least 100 times as small as that of the recording layer. Supports whose resistivity is not higher than $10^7$ ohm.cm are preferred. The recording layers themselves have preferably an electrical insulating power as high as possible without affecting too much the photosensitivity by means of too high an amount of insulating binding agent. Preferably the recording layers have in non-irradiated state (i.e., dark-adapted state) a resistivity of at least $10^9$ ohm.cm.

Suitable conductive plates are, e.g., plates of metals such as aluminium, zinc, copper, tin, iron, or lead.

Suitable electro-conductive interlayers for insulating supports are, e.g., vacuum-coated metal and conductive metal compound (metal oxide or metal salt) layers such as siler, tin, aluminium, titanium dioxide and copper iodide conductive layers, transparent conductive polymer layers, e.g. applied from polymers containing quaternized nitrogen atoms, such as those described in the United Kingdom patent specification No. 950,960 filed Sept. 23, 1960 by Gevaert Photo-Producten N.V., or layers containing conductive particles, e.g. carbon black and metal particles dispersed in a binder. The binder used for said particles has a resistivity preferably lower than $10^6$ ohm.cm. A suitable binder for that purpose is gelatin.

It is possible to produce transparent photoconductive recording materials by applying the photoconductive compounds together with a suitable binder (if necessary) from a clear solution to a conductive transparent base or a transparent insulating base coated with an electroconductive transparent interlayer.

As transparent bases resin sheets having an optical density of not more than 0.10 are preferred, e.g., a sheet made of polyethylene terephthalate or cellulose triacetate. The conductive interlayer preferably consists of a metal coating, e.g., a vacuum-coated aluminium layer having an optical density of not more than 0.30, or of a conductive transparent polymer layer composed, e.g., of an organic polyionic polymer, e.g. a polymer containing quaternized nitrogen atoms such as a quaternized polyethylene-imine.

In reproduction techniques wherein the prints are to be produced on an opaque background preferably a paper sheet is used as support for the recording layer.

Paper sheets that have an insufficient electrical conductivity are coated or impregnated with substances enhancing their conductivity, e.g. by means of a conductive overcoat such as a metal sheet laminated thereto.

As substances suited for enhancing the conductivity of a paper sheet and which can be applied in the paper mass are particularly mentioned hygroscopic compounds and antistatic agents as described, e.g., in the United Kingdom Patent Specification 964,877 filed May 2, 1960 by Gevaert Photo-Producten N.V., and antistatic agents of polyionic type, e.g. CALGON CONDUCTIVE POLYMER 261 (trade mark of Calgon Corporation, Inc. Pittsburgh, Pa., U.S.A.) for a solution containing 39.1% by weight of active conductive solids, which contain a conductive polymer having recurring units of the following type:

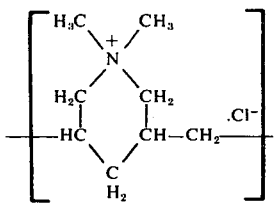

Paper sheets are preferably impermeabilized to organic solvents, e.g. by means of a water-soluble colloid or by strongly hydrating the cellulose fibers such as in the case of glassine paper.

In order to prepare an electrophotographic material according to the present invention various techniques may be applied.

In practice, the photoconductive substances involved, either alone or together with other additives such as those described above, preferably are first dissolved or dispersed in a suitable organic solvent such as a chlorinated hydrocarbon, e.g. methylene chloride. The solution or dispersion thus obtained is uniformly spread on a surface of a suitable support, e.g. by centrifuging, spraying, brushing, or coating. Thereupon the layer formed is dried in such a way that a solid photoconductive layer is formed on the surface of the support.

Recording materials according to the present invention can be used in any of the different techniques known in recording with the aid of photoconductors. According to a preferred embodiment they are used in a technique base on the discharge of an electrostatically charged recording layer by exposure to light.

Photoconductive recording materials prepared according to the present invention can be used in exposure unit equipped with incandescent lamps, so that they need not be exposed with light rays rich in ultraviolet such as those emitted by a high-pressure mercury vapour bulb.

The electrostatic charging of photoconductive recording elements according to the present invention can be effected according to any method known in electrophotography, e.g. by friction with a smooth material, with a material possessing a high electric resistance, e.g. a cylinder coated with polystyrene, by corona discharge, by contact charge, or by discharged of a capacitor.

Recording materials containing the said organic photoconductive substances can be used in a recording technique comprising a negative corona charging as well as in a recording technique comprising a positive corona charging.

In order to obtain an electrostatic image it is possible to effect the charging and exposure steps simultaneously and even to expose the recording layer image-wise before charging since a conductivity image is formed that is not destroyed immediately, especially if diazonium salts are used in the recording element. It is preferred, however, that the charging is effected before image-wise exposure.

The electrostatic latent image can be converted into a visible image either on the electrophotographic material wherein the latent image was formed, or on a material to which the electrostatic latent image was transferred, e.g. by application of the method described in the Belgian Patent Specification No. 529,234 filed May 29, 1954 by Chester Floyd Carlson.

The conversion of the original or transferred latent image into a visible image can occur according to one of the techniques known in electrophotography, wherein use is made of a conductivity pattern (e.g. electrolysis) or the electrostatic attraction or repulsion of finely divided coloured substances, which, e.g., are present in a powder mixture, in an electrically insulating liquid (e.g. in the form of a suspension) or in a gas (e.g. in the form of an aerosol), or wherein electrostatic attraction is used for selectively wetting charged portions of the recording layer, as described in the United Kingdom patent specifications Nos. 1,020,505 filed Nov. 8, 1961 and 1,033,419 filed Nov. 26, 1962 both by Gevaert Photo-Production N.V.

When the sign of the charge of the developing powder or developing liquid is properly chosen, either a negative or a positive print can be obtained from any original. If both printing material and developing powder or developing liquid have the same sign of charge, the powder only adheres to the discharged areas so that a negative print is obtained. If the signs of the recording material and of the developing powder or developing liquid differ, a positive print is obtained.

If a coloured powder is used for making visible the latent image, the visible image obtained can, if necessary, be fixed according to one of the methods known in electrophotography, e.g., by heating, or it can be transferred to another support, e.g. according to the method described in the United Kingdom patent specification No. 658,699 filed Apr. 14, 1949 by Battelle Memorial Institute and fixed thereon.

The present heterocyclic organic photoconductive compounds can also be supplied in a thermoplastic recording process to form a ripple-image as described, e.g., in the United Kingdom patent specification No. 964,881 filed May 17, 1960 By Gevaert Photo-Production N.V.

Evidently the present invention by no means is limited to one or other particular embodiment of using the electrophotographic material containing the photoconductive compounds as described herein. The exposure technique, the charging method, the formation of the charge pattern, the transfer of such pattern if applied, the developing method, and the fixation or the transfer of the developing material pattern may be modified or adapted.

The composition of the recording materials used in these methods may be adapted to the requirements of the recording process used.

Electrophotographic materials according to the present invention can be employed in reproduction techniques, wherein different kinds of electromagnetic radiations are used, e.g. visible light, U.V.-radiation, X-rays and γ-rays.

The following examples illustrate the present invention.

EXAMPLE 1

To a polyethylene terephthalate support of 100 μ a conductive transparent coating was applied from an aqueous solution of gelatin and GALGON CONDUCTIVE POLYMER 261 (trade name) in a weight ratio of 2:1. The coating was carried out in such a way that the dried coating contained 2 g. of gelatin per sq.m. The electrical resistivity of the coating was $5\times10^6$ ohm per sq.cm.

An electrophotographic recording material was prepared by coating onto said conductive layer a solution containing:

| | |
|---|---|
| one of the photoconductive compounds listed in Table I or II | 3 g |
| copoly(vinyl chloride/vinyl acetate/ maleic anhydride) (mol ratio: 86.5/13.3/0.2) | 5 g |
| methylene chloride | 100 ml |

The solution was applied in such a ratio that the dried recording layer contained 3 g per sq.m of said photoconductive compound.

After a negative corona charging with a potential difference of - 6000 v. between the corona wires and the ground, the charged recording layer was contact-exposed for 30 sec. through a step wedge of increment 0.2 with incadescent bulbs that together represent 100 w. and were placed at a distance of 30 cm.

After exposure the development was carried out with an electrophoretic developer containing positive toner particles and which was prepared by diluting the concentrated developer composition described hereinafter in a volume ratio of 15/1000 by means of ISOPAR H (trade name for an isoparaffinic hydrocarbon mixture having a boiling range of 177°–188°C sold by Esso Belgium, N.V., Antwerp, Belgium):

| | |
|---|---|
| carbon black (average particles size:20 μ) | 30 g |
| zinc monotridecyl phosphate as dispersing agent | 1.5 g |
| ISOPAR H (trade name) | 750 ml |
| resin solution prepared as described hereinafter | 150 g |

The resin binder solution was prepared by heating 500 g. of ALKYDAL L 67 (trade name of Farbenfabriken Bayer A.G., Leverkusen, W. Germany, for a linseed oil-modified (67% by weight) alkyd resin) and 500 ccs. of white spirit containing 11% by weight of aromatic compounds at 60°C. till a clear solution was obtained, and subsequent cooling.

The relative speed values of the developed samples were calculated on a percentage basis taking into account a comparison of the number of visible steps obtained in the different wedge images with the number of visible steps in the wedge image of the sample containing compound 4 of Table II.

The following Table IV lists the relative speed values from these coatings.

Table IV

| No. of the photoconductive compound of Table I or II | Relative Speed |
|---|---|
| I, 1 | 10 |
| I, 2 | 10 |
| I, 3 | 10 |
| II, 1 | 160 |
| II, 2 | 100 |
| II, 3 | 100 |
| II, 4 | 100 |
| II, 5 | 1,000 |
| II, 6 | 100 |
| II, 7 | 100 |

EXAMPLE 2

Photoconductive coatings were prepared from the following compositions A and B.

| Ingredients | Composition A | Composition B |
|---|---|---|
| photoconductive compound 4 of Table II, | 6 g | 6 g |
| phthalic anhydride | 0.25 g | — |
| copoly(vinylchloride/vinylacetate maleic anhydride) (mol ratio: 86.5/13.3/0.2) | 4 g | 4 g |
| sym.-dichloroethane | 90 ml | 90 ml |
| dimethylformamide | 10 ml | 10 ml |

The compositions were coated as described in Example 1, and the dried coatings under the same conditions negatively coronacharged, exposed through a step-wedge with increment 0.2 and electrophoretically developed as described in Example 1.

Compared with the speed value of coating B the speed of the chemically sensitized coating A was 2.5 times as high.

EXAMPLE 3

The following composition was coated on an aluminium-laminated paper:

| | |
|---|---|
| Compound 1 of Table II | 6 g |
| Copoly(vinyl chloride/vinyl acetate/ maleic anhydride) (mol ratio:86.5/ 13.3/0.2 | 4 g |
| As spectral sensitizing agents: Orange Astrazon R (C.I. Basic Orange 22; C.I. 48,040) having the following structural formula: | |

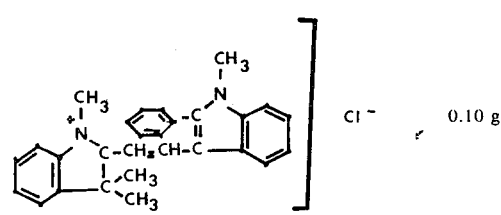

0.10 g

Brillant Green YS (C.I. Basic Green 1; C.I. 42,040) having the following structural formula:

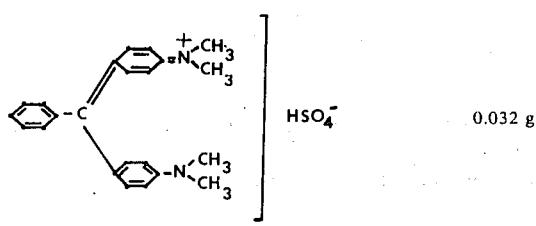

HSO$_4^-$    0.032 g

Rhodamin B (C.I. Basic Violet; C.I. 45,170) having the following structural formula:

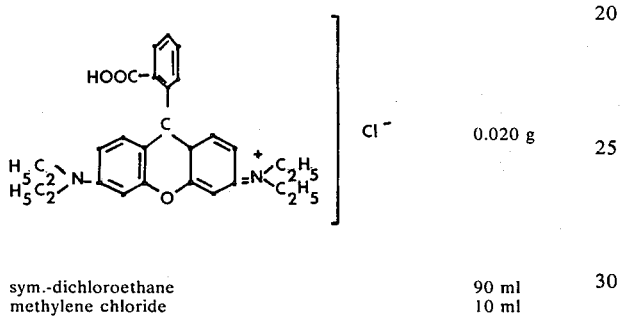

Cl$^-$    0.020 g

| | |
|---|---|
| sym.-dichloroethane | 90 ml |
| methylene chloride | 10 ml |

The coating was carried out in the way described in Example 1.

The dried coating was negatively corona-charged with a potential difference of - 6000 V between the corona wires and the ground. The charged recording layer was contact-exposed for 5 sec. through a step-wedge having an increment 0.2 using tungsten filaments lamps that together represent 100 W and were placed at a distance of 30 cm.

The electrophoretic development was carried out as described in Example 1. Compared with a same non-spectrally sensitized coating the total sensitivity of the spectrally sensitized coating was 40 times as high.

EXAMPLE 4

To the coating composition of Example 3, 0.25 g of 2,3-dicyano-p-quinone was added as chemical sensitizing compound with strongly electronegative groups.

The corona charging, image-wise exposure and development were the same as in Example 3. The speed of the recording layer was found to be 3 times as high as that of Example 3.

EXAMPLE 5

A photoconductive recording material as described in Example 1 was prepared with the difference, however, that the photoconductive compound had a structure as defined hereinafter in connection with the preparation.

The processing of said photoconductive material was the same as explained in Example 1. The relative speed derived from the developed sample corresponded with the value 160.

Preparation of the photoconductor having the structural formula:

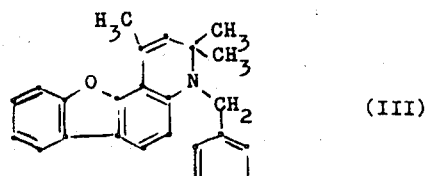

according to the following reaction scheme:

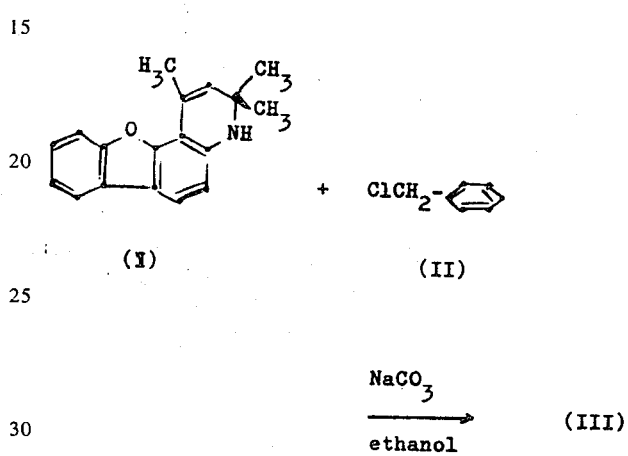

Synthesis of compound (I)

A mixture of 0.25 mole of 2-amino-diphenylene oxide, 1 g of iodine and 2 mole of mesityloxide was heated for 12 h on an oilbath of 140°C. The acetone produced in the reaction was separated through a dephlegmator.

The obtained reaction mixture was subjected to diminished pressure to remove the volatile products. The residue was dissolved in methylene chloride and washed in subsequent order:

3 times with 5N aqueous hydrochloric acid, 3 times with an aqueous 30 % by weight sodium hydroxide solution, 3 times with water.

The methylene chloride was purified by column chromatography using a column provided with silica gel as adsorbent and as eluent a mixture of methylene chloride/benzene (8:2 by volume). This purification was repeated twice. Yield : 5 g. Oily product.

Synthesis of compound (III)

0.2 mol of compound (I) were dissolved in 200 ml of anhydrous ethanol and mixed with 0.6 mol of benzylchloride [compound (II)] and 0.22 mol of calcined sodium carbonate.

The reaction mixture was kept boiling under reflux for 10 h. The reaction mixture was subjected to filtration and the solvent removed from the filtrate by evaporation. The solid residue was rubbed in a petroleum fraction boiling between 40°–120°C whereby the residue was partially dissolved. The obtained solution was boiled with 40 g of silica gel, subsequently cooled down, the silica-gel removed by suction and the filtrate subjected to evaporation. The solid product left was further purified by dissolution and precipitation from n-hexane and finally recrystallized from said petroleum fraction in the presence of activated carbon. Melting point: 141°C. Yield : 12 %.

We claim:
1. A chemical compound corresponding to the following formula:

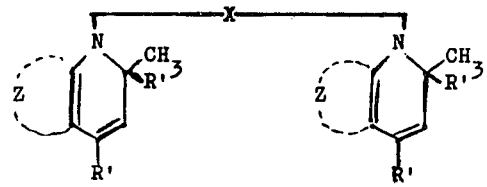

wherein:
Z represents the necessary atoms to close and adjacent benzene or fluorene nucleus or,
R' represents ($C_1$-$C_4$) alkyl, and
X represents $CH_2$-$CH_2$ or

2. A chemical compound according to claim 1, wherein Z represents the necessary atoms to close a fluorene nucleus, R' is methyl and X is an ethylene group.

* * * * *